United States Patent [19]
Shattuck et al.

[11] Patent Number: 5,536,172
[45] Date of Patent: Jul. 16, 1996

[54] QUANTIFICATION OF PHOTOREACTIVE AROMATIC COMPOUNDS

[75] Inventors: Meredith D. Shattuck, Providence; Stephen B. Turcotte, Logan, both of Utah

[73] Assignee: Utah State University, North Logan, Utah

[21] Appl. No.: 372,287

[22] Filed: Jan. 13, 1995

Related U.S. Application Data

[62] Division of Ser. No. 69,625, Jun. 1, 1993, Pat. No. 5,427,955.

[51] Int. Cl.$^6$ ................................................ G01N 33/00
[52] U.S. Cl. .......................... 436/140; 436/124; 436/125; 436/126; 436/139; 436/171; 436/177
[58] Field of Search ................................ 436/124–126, 436/139–140, 171, 177

[56] References Cited

U.S. PATENT DOCUMENTS

| | | | |
|---|---|---|---|
| 2,385,471 | 7/1941 | Scharer | 23/230 |
| 4,891,322 | 1/1990 | Blackburn et al. | 436/140 X |
| 4,992,379 | 2/1991 | Hanby | 436/210 |
| 5,028,543 | 7/1991 | Finch | 436/124 |

OTHER PUBLICATIONS

M. A. Slifkin et al, *Nature* 1967, 215, 949–950.
R. B. Zhutkovskii et al, *Chem. Abstr.* 1974, 80, 151039x.
R. V. Pole et al, *Appl. Phys. Lett.* 1976, 28, 494–497.
J. K. McVey et al, *J. Chem. Phys.* 1976, 65, 3375–3376.
F. A. Carroll et al, *J. Phys. Chem.* 1976, 80, 2046–2047.
G. Vermeersh et al, *Chem. Abstr.* 1979, 90, 54180k.
N. Selvarajan et al, *Ind. J. Chem.* 1979, 18A, 23–26.
M. P. Fogarty et al, *Appl. Spectrosc.* 1980, 34, 438–445.
O. V. Butrimovich et al, *Chem. Abstr.* 1980, 93, 158163k.
F. De Wiest *Chem. Abstr.* 1981, 95, 23851d.
V. A. Borovkova et al, *Chem. Abstr.* 1981, 95, 61015s.
J. M. Masnovi et al, *Can. J. Chem.* 1984, 62, 2552–2559.
M. Okamoto et al, *J. Phys. Chem.* 1984, 88, 5644–5646.
L. G. Aravin et al, *Chem. Abstr.* 1984, 101, 219599q.
J. Stauff et al, *Chem. Abstr.* 1986, 105, 171596q.
N. A. Sadovskii et al, *Chem. Abstr.* 1988, 108, 46660s.
V. A. Lyubimtsev et al, *Chem. Abstr.* 1988, 109, 159344f.
S. A. Tucker et al, *Appl. Spectrosc.* 1990, 44, 269–273.
W. M. Wiczk et al, *Z. Naturforsch* 1986, 419, 761–766.
W. M. Wiczk et al, *Z. Naturforsch.* 1987, 429, 1290–1295.
W. M. Wiczk et al, *Z. Naturforsch* 1991, 469, 259–264.
F De Wiest *Atmos. Environ.* 1981, 15, 407–409.
W. C. Meyer, "Halogen–Sensitized Photoionization of N,N, N',N'–Tetramethyl–p–phenylenediamine in Liquid Halogenomethanes," J. Physical Chemistry, vol. 74, No. 10, pp. 2118–2121, 1970.
W. C. Meyer, "Halogen–Sensitized Photoionization of Aromatic Amines in Molded Polymer Films," J. Physical Chemistry, vol. 74, No. 10, pp. 2122–2126, 1970.
W. C. Meyer, "Correlation of the Luminescence Perturbation of N,N,N',N'–Tetramethyl–p–phenylenediamine with the Path of Halogen–Sensitized Photoionization," J. Physical Chemistry, vol. 74, No. 10, pp. 2127–2132, 1970.

*Primary Examiner*—Arlen Soderquist
*Attorney, Agent, or Firm*—David B. Denoyer; Eleanor V. Goodall; Jon C. Christiansen

[57] ABSTRACT

A method for determining the amount of photoreactive polynuclear aromatic compound in a sample is described. A sample containing an unknown amount of a photoreactive polynuclear aromatic compound is mixed with a known quantity of a polyhalogenated organic compound and exposed to light of a known wavelength for a known length of time. The quantity of the photoreaction product which results from the light exposure is measured by absorption spectroscopy. Comparison of the absorption measurement to a standard curve allows determination of the concentration of the photoreactive aromatic compound. The simplicity of the method makes it suitable for on-site testing. The method can be used to test for photoreactive compounds in various media, such as soil, aqueous samples, and oil.

5 Claims, 7 Drawing Sheets

QUANTIFICATION OF PHOTOREACTIVE AROMATIC COMPOUNDS

This application is a division of application Ser. No. 08/069,625 filed Jun. 1, 1993, now U.S. Pat. No. 5,427,955.

BACKGROUND OF INVENTION

A. The field of the Invention

This invention concerns a method for detecting quantities of halogenated organic compound content in samples of contaminated material, for example, soil, oil, or water. The method can also be applied to determine the presence of a quantity of selected aromatic compounds by using halogenated hydrocarbons in known concentrations.

B. The Background Art

Halogenated hydrocarbons find many uses in industry as intermediates in the manufacture of organic compounds, and are directly useful in applications such as cleaning solvents and wood preservatives. Halogenated hydrocarbons are recognized hazards when released into the environment, for example, when polychlorinated biphenyls used in dielectric fluids leak from transformers. The United States Environmental Protection Agency mandates testing for halogenated hydrocarbons by complicated methods. For example, one method involves gas chromatography, which directly tests for the presence of halogenated compounds using expensive analytical instruments.

Field tests for aromatic contaminants have been described. For example, U.S. Pat. No. 4,992,379 describes the use of Friedel-Crafts Lewis acid catalysts to produce a colored product useful in the characterization of aromatic contamination. However, the above field test is different from the present invention in several respects, including underlying chemical reaction, method of application, and flexibility.

SUMMARY OF THE INVENTION

The invention disclosed provides a method for measuring the halogenated organic compound, or organic halide content of a sample. The method can be used for detecting impurities in a solid or liquid sample, for example, soil or oil. An object of the invention is to provide a simple and inexpensive method for identifying the presence of toxic halogenated organic impurities. These impurities are present in soil and oil samples surrounding various industrial and consumer applications using halogenated organic compounds such as carbon tetrachloride and pentachlorophenol.

The present invention incorporates the discovery that ionization of certain reagent dyes, such as aromatic amine dye compounds, is induced by light excitation of the reagent dye. It has been discovered that through proper choice of reagent and solvent used to mix the reagent, the reaction will not measurably occur unless halogenated organic compound is present during light exposure. This makes the method of the present invention useful for controlled identification and measurement of a variety of halogenated compounds, and certain aromatic compounds. Because of the distinctive spectra or color of a particular reagent when contacted with a particular contaminant compound and exposed to light, the method is useful for identification of halogenated compounds in varied media, such as soil, aqueous samples, and oil. Additional flexibility in the method is obtained because of the ability to control the light energy used for facilitation of the reaction used in the invention.

The method involves contacting an energy sensitive reagent, such as an aromatic amine molecule, and a sample containing a quantity of halogenated organic compound, such as halogenated hydrocarbon ("HHC"). Exposure to light causes a color change dependant on several variables, including the concentration of HHC. The resulting absorbance change can be measured to quantify the concentration of the HHC. The photodonor reagent, or photoindicator performs the role of a concentration indicator. The change in the reagent can be quantified visually or spectrophotometrically, depending on the specific reagent. The change in absorbance of the exposed photoindicator reagent varies, depending on the choice of photoindicator reagent, solvent used to dissolve the photoindicator, and the contaminant contacted. Our invention incorporates the discovery that for many contaminants, the light induced change in absorbance of the system is proportional to the contaminant concentration.

In another aspect of the present invention the roles of the organic halide and the photoindicator can be reversed to determine the presence or quantity of aromatic compounds which are sensitized by the presence of halogenated organic compounds. In this aspect of the invention, a known quantity of organic halide is mixed with a sample contaminated with aromatic contaminant. Aromatic molecules, such as pyrene, which are sensitive to the light induced changes caused by the presence of halogenated organic compounds can then be detected in contaminated samples by the method of the present invention. This is a reversal of the previous embodiment of the invention, which used a constant concentration of aromatic compound to quantify halogenated organic compounds

BRIEF DESCRIPTION OF THE DRAWINGS

FIG. 2 represents a calibration curve of reference data.

DETAILED DESCRIPTION OF THE INVENTION

Figure 1:
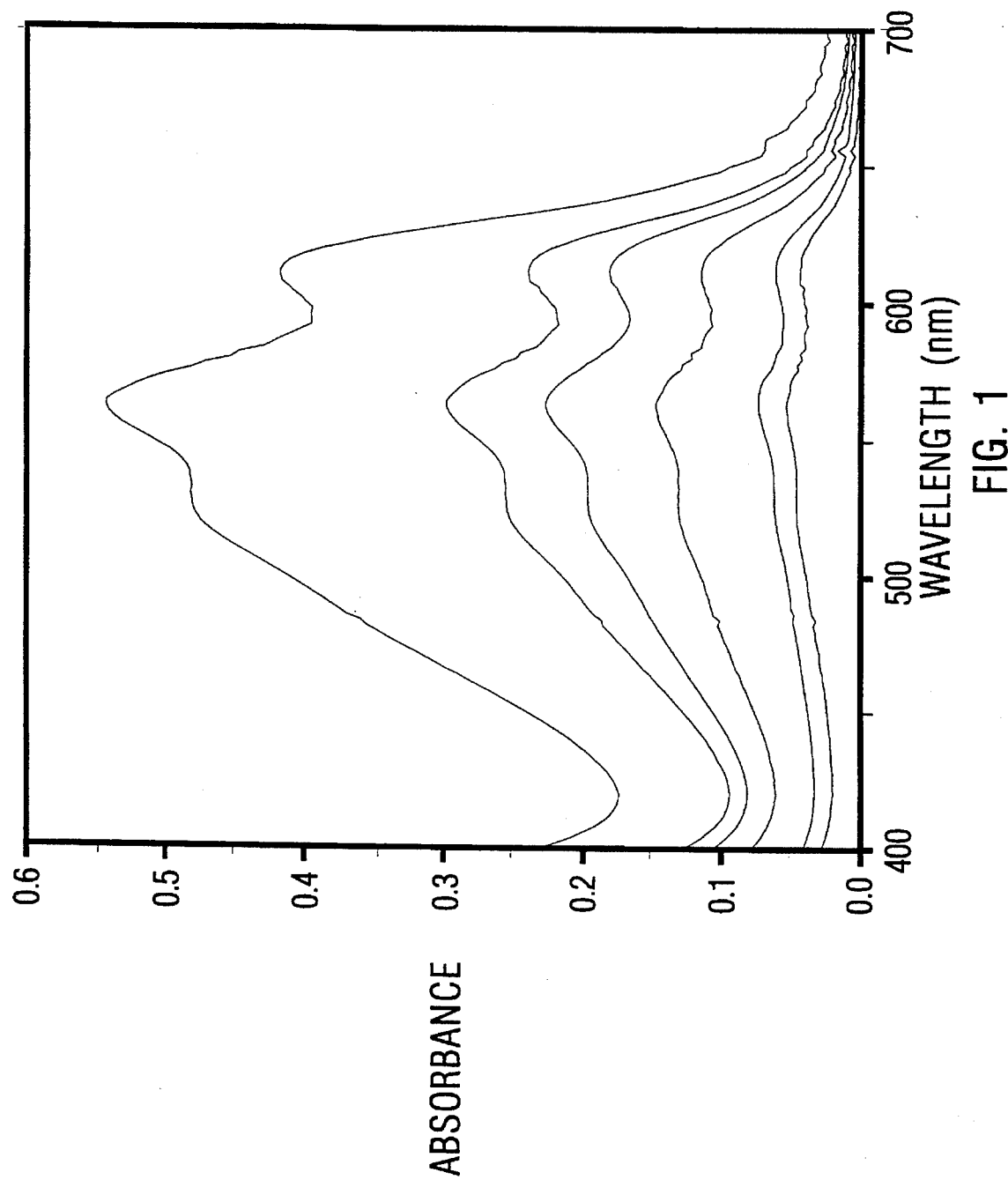
FIG. 1 depicts data produced from application of the method to a system comprising N,N,N',N'-tetramethyl-p-phenylenediamine ("TMPD") reagent mixed in isopropyl alcohol. The y-axis represents absorption and the x-axis represents wavelength in nanometers. The traced lines represent the absorbance of samples containing pentachlorophenol as a contaminant after exposure to ultraviolet light for thirty minutes. In ascending order of absorbance values, the respective concentrations of pentachlorophenol in parts per million are 0, 1.0, 5.1, 11.1, 22.2, and 44.3.

The method of the present invention is based on a color producing reaction that occurs between halogenated organic compounds and reagents such as aromatic amine compounds. The term photodonor is used to describe reagents that are used in the invention. The reagents act as indicators when contacted with halogenated organic compounds while exposed to light. For a given reagent, exposure to light of a sufficient intensity for an appropriate amount of time will produce changes in the absorption of the reagent.

The present invention incorporates the discovery that the changes in the absorption of a properly selected reagent depend on light exposure, and the concentrations of both reagent and halogenated hydrocarbon. Therefore, by holding the concentration of reagent and time of light exposure steady, halogenated hydrocarbon can be detected and quantified through observations of absorbance changes. This light absorption data is measured after contacting the reagent and contaminant and exposing the contacted reagent to light. Likewise, by holding the concentration of halogenated hydrocarbon and time of exposure constant, polyaromatic organic compounds which react with the selected HHC may be quantified.

A useful feature of the method is that by proper choice of reagent and solvent used to dissolve the reagent or dilute the sample, no substantial absorbance change will occur until the reagent is sensitized by the presence of halogenated compounds and exposed to light. The method is useful in determining the presence of aliphatic halogenated compounds including carbon tetrachloride and chloroform. Aromatic halogenated compounds such as chlorinated phenol compounds are also detectible under this method. Other detectible contaminants include complex halogenated polyaromatic compounds such as polychlorinated and polybrominated biphenyl compounds.

By adjusting the reagent type, solvent type, and energy or light exposure level, sensitivity levels can be adjusted to detect various concentrations of contaminants in a variety of sample media. For instance, if a lower detection threshold is desired, light intensity and exposure time could be increased. Conversely, if higher quantities of contaminant are present in a sample, dilution with a properly selected solvent produces a useful application of the invention.

In one optimized application of the method of the present invention, reagent and solvent are matched. The objective of this solvent match is to create a system requiring the presence of halogenated hydrocarbon and exposure to energy to produce absorption changes in the exposed system. The preferred system is substantially unchanged in absorbance when exposed to light in the absence of halogenated hydrocarbon. Some changes in reagent absorption in the absence of halogenated hydrocarbon can be tolerated. For instance, light induced reagent absorption change in the absence of contaminant is one type of background absorption which can be tolerated. For example, an adjustment can be made by subtracting the background change in absorption from observed levels in contaminated samples.

Background absorbance changes may occur when reagent and solvent are mixed and exposed to light, in the form of sunlight, or artificial ultraviolet light. We have found that the polarity, or dielectric constant of the solvents used to dissolve the photodonor reagent is a factor in the background absorption of the system and may also change the rate of reaction between photodonor reagent and halogenated organic compounds. By experimentation we have found that mixing the photodonor reagent with a solvent, exposing the mixture to a light source, and measuring the absorbance will provide data for photodonor reagent-solvent matches that minimize background changes.

Because the polarity of solvent used to dissolve the reagent used may cause variations in the reactions between reagent and halogenated organic compound it is important to determine reference data over a range of halogenated organic compound concentrations. For instance, when the method of the present invention is used to quantify pentachlorophenol ("PCP") concentration by using a system of N,N,N',N'-tetramethyl-p-phenylenediamine ("TMPD") reagent in methanol solvent, a high background level of absorbance is observed for exposed solvent and reagent in the absence of halogenated hydrocarbon.

While the instant invention may be incorporated in various methods for detecting and determining the amount of halogenated and aromatic compounds in several media, such as soil, oil, or solutions, the examples described herein use known chlorinated hydrocarbons and polyaromatic hydrocarbons.

DETERMINING REFERENCE DATA

The analytical method of the present invention utilizes a comparison of reference data and light absorbance data from a contaminated sample. Therefore, the system described herein discloses a method for generating reference data. Reference data is produced by contacting a known concentration of photoreactive reagent compound with known concentrations of a contaminant such as halogenated hydrocarbon. A series of contaminant concentrations may be used. These known mixtures are exposed to light for a measured period of time, and the resultant changes in optical absorption are documented. For example, we have effectively used spectrophotometry to determine reference data for reagents contacted with known halogenated organic compounds. The reference data can then be used to determine the presence of quantities of halogenated organic compounds in a test sample. In many cases the method provides a means to identify compounds by comparing experimentally generated light absorption data with reference data.

The method of the invention incorporates several variables that influence the magnitude of absorption changes. The chemical characteristics of a particular halogenated organic to be detected is a major factor in the shape and magnitude of the measured absorption changes. In addition, the polarity of solvents used to dissolve reagent or extract a sample influence changes in absorption. In addition, light intensity, time of exposure, and time of measurement may influence changes in the measured light absorption. These variables are controlled when generating reference data.

An initial step in determining reference data is the step of determining a wavelength appropriate for the reagent-contaminant system. For example, the reagent to be used is contacted with the desired halogenated hydrocarbon contaminant in a known concentration, exposed to light for a measured amount of time, and spectrophotometrically analyzed over a range of wavelengths. This spectrum provides an optimum wavelength for peak sensitivity facilitating efficient identification of contaminant concentration by maximizing the observable changes in light induced absorption changes.

In addition, the signature shape of the reference plot of absorption versus concentration of contaminant can be used to identify the contaminant in a sample. The signature shape is characterized by noting the magnitude and wavelength in the spectral data of an exposed, contacted reagent, over a range of wavelengths. In specific cases, we have found that some classes of contaminants are generally identifiable by the shape of the signature absorbance plot. This finding has allowed us to differentiate aliphatic and aromatic contaminants in specific reagent-contaminant cases.

One method of determining reference data for an exposed, contacted reagent comprises measuring the post-exposure absorbance of a series of aliquots containing fixed concentration of a reagent. In order to determine a background absorption for non-contacted reagent, an aliquot containing a fixed quantity of reagent without contaminant is prepared. Other aliquots are prepared with varying concentrations of a contaminant. All samples are exposed to light, and absorbance is measured at the previously determined optimized wavelength. The portion of absorbance change attributable to the contaminant can then be measured.

Alternatively, the steps of absorbance optimization and calibration of known concentrations of contaminant can be performed in a single analysis by measuring the absorbance of each aliquot containing over a range of wavelengths as shown in FIG. 1. This reference step provides data to establish a minimum contaminant detection level for a given contaminant-reagent system. It is important to note that by measuring the absorbance of an aliquot containing only reagent and solvent used, the background level of the light exposed reagent-solvent system, if any, is determined. Another background absorbance to be considered when appropriate is the background level of absorbance of the reagent-solvent-contaminant system prior to light exposure. This pre-exposure type of background level is illustrated by the lower absorbance plot of FIG. 3. The goal of the reference data step is to isolate the portion of light induced increase in absorption that is attributable to the presence of halogenated hydrocarbon.

As stated above, reference data can be used to identify certain classes of halogenated hydrocarbons. For instance, plots containing broad peaks, having an increase in absorption over a relatively large range of wavelengths are characteristic of complex aromatic halogenated compounds such as 2,2',4,5-tetrachlorobiphenyl. In contrast, data from a similar reagent system contacted with aliphatic compounds such as carbon tetrachloride exhibits less linewidth in the plot of reference data. The plot is more of a spike, occurring over less wavelength range. Data from compounds with bonds of an intermediate nature are exemplified by reference data generated from trichloroethylene as a sample, producing peaks of an intermediate linewidth when compared to the above aromatic and aliphatic compounds. Thus, the linewidth of the reference data can be used to characterize the contaminant. This generalization is limited to specific reagent-solvent systems. By specific experimentation and application of the method of the invention, various contaminant classes are identifiable.

The production of reference data can also facilitate delayed measurement of a contaminant in a sample, by measuring the amount, if any, light induced absorption decays with time after exposure. We have found that when the method is applied using certain reagents, light induced increases in absorption decrease, or decay, with time after exposure. Therefore it can be important to control the time between light exposure and measurement of optical absorption. For these systems it is important to determine whether changes in the reagent system persist, or decay over time. Thus, for some reagents, both the time of exposure and time of measurement should be controlled variables. Therefore, time dependent changes in absorption, if any, should be incorporated into both the reference and sample data measurements of the method. In addition, some systems may produce absorbance changes in the solvent-reagent system prior to contact with contaminant. In these systems, both the timing of reagent-contaminant contact and time of solvent and reagent mixing are important variables to control.

APPLICATION OF THE METHOD

Reagents used as photoindicators are compounds that undergo change in light absorption, or change in color, in the presence of contaminant and exposure to the correct amount of energy, for example, light of sufficient intensity and wavelength to promote the reaction. Preferred photoindicators include 2,7-diaminofluorene and N,N,N',N'-tetramethyl-p-phenylenediamine ("TMPD").

We have discovered that background coloration of a some reagent photoindicators can be controlled by the solvent in which the photoindicator is dissolved. This background coloration refers to the tendency of some photoindicators to change color upon exposure to light in the absence of HHC. Thus, with proper match between photodonor reagent and solvent, no change in absorbance is produced unless a contaminant is present. A preferred match of solvent is exemplified by a solution of TMPD in isopropyl alcohol. Other preferred matches are provided by mixing the photoindicator 1-phenyl-3-p-diethylaminostyryl-5-p-diethylamino-phenyl-2-pyrazoline ("DEASP") in acetonitrile and 2,7-diaminofluorene mixed in isopropyl alcohol.

Once reference data has been determined for a system of reagent and a contaminant, the reference data can be used to determine the concentration of contaminant in a test system through comparison of light induced changes in absorbance. It is important to note that the comparison is made by determining the difference between pre-exposure sample absorbance and post-exposure sample absorbance. In this way, any absorption increase is due to light induced changes.

Contacting the reagent and contaminant to produce light induced change can occur in the sample, or alternatively, the contaminant can be separated prior to contact with the reagent. Another variation of the method includes separating the reagent and contaminant after contact and prior to exposure to light. A similar variation includes separating the contacted reagent after exposure.

EXAMPLE I

Figure 2:
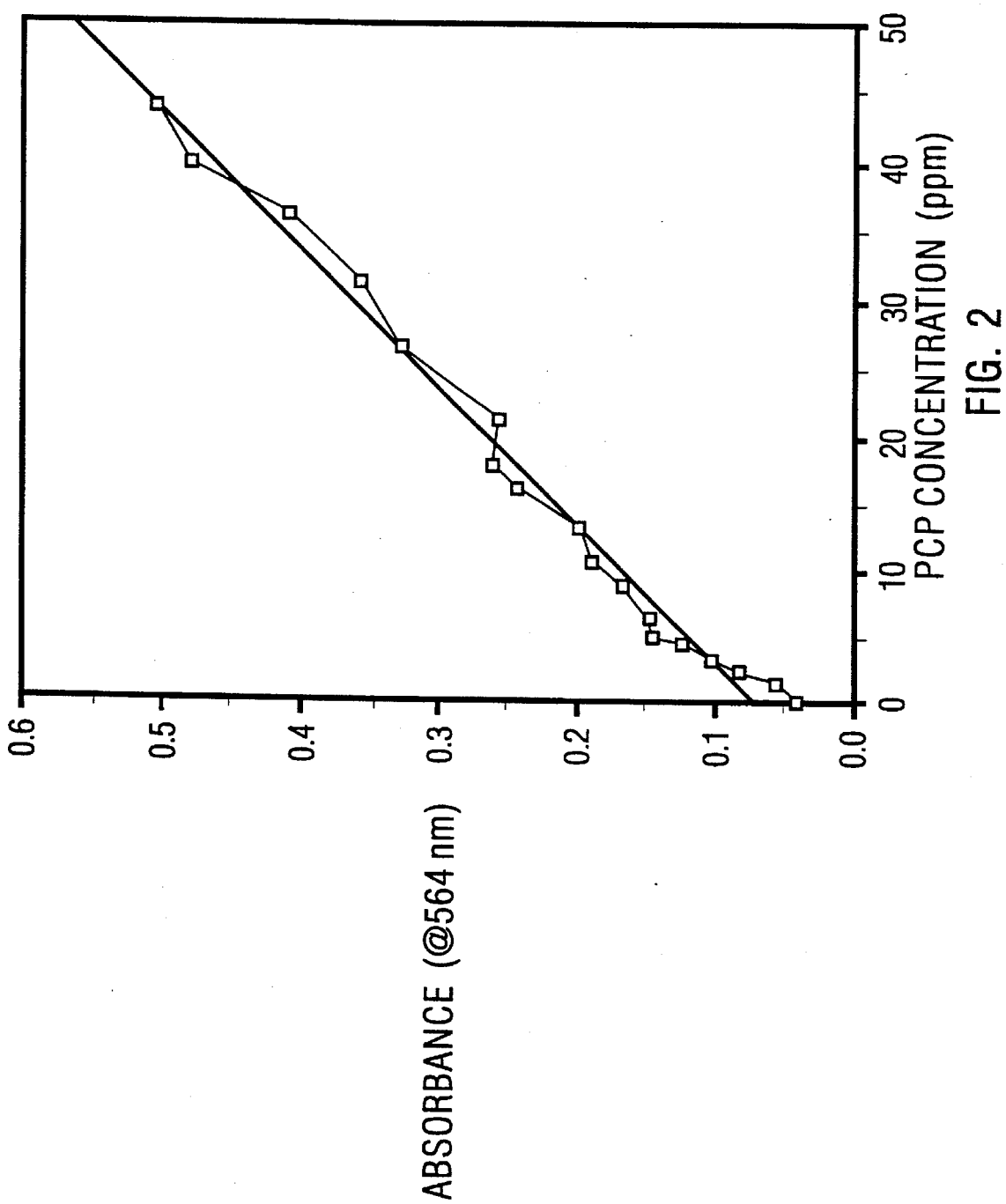
FIG. 2 depicts a plot of the data from FIG. 1, using the x-axis to represent pentachlorophenol concentration.
Figure 3:
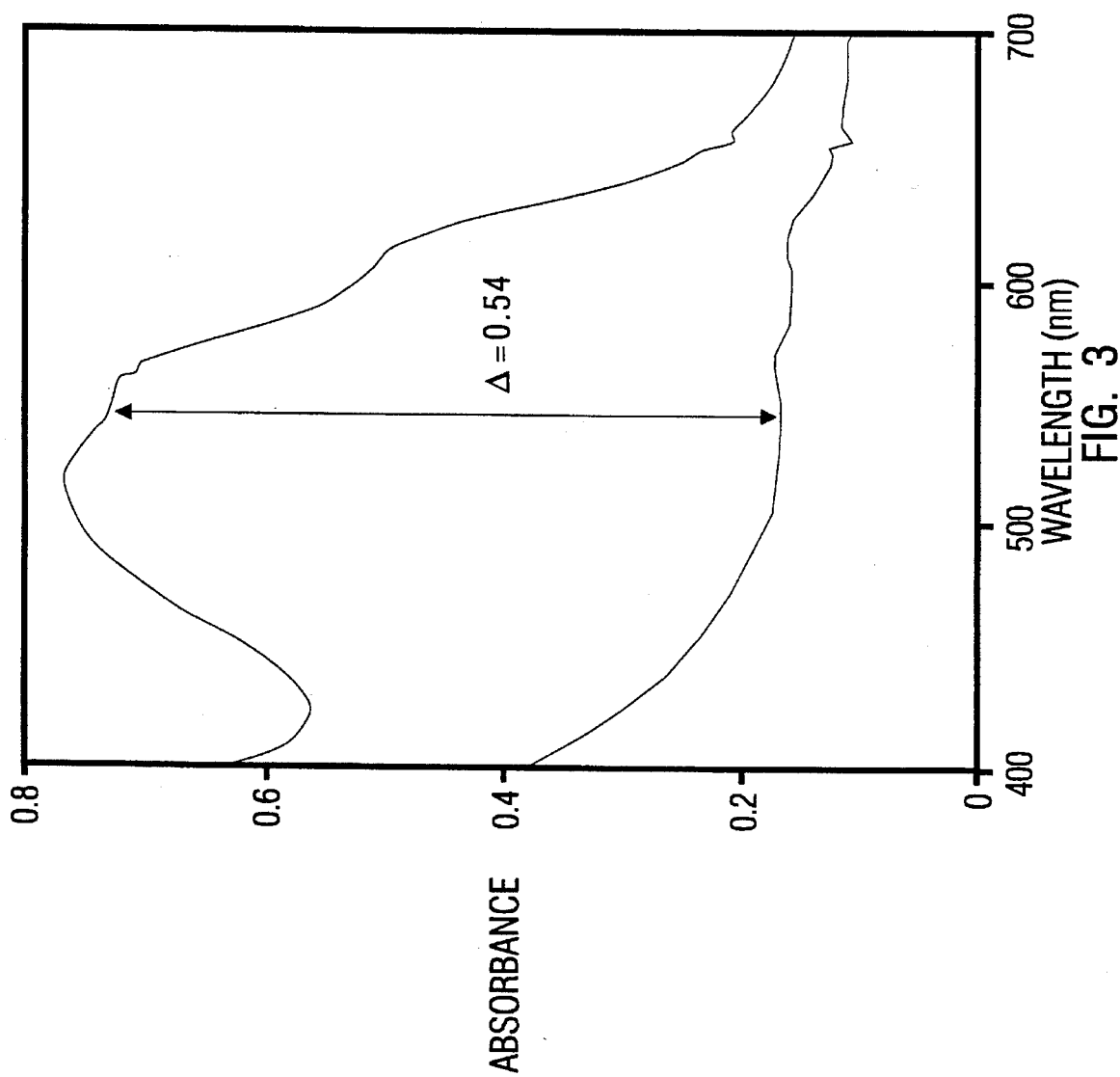
FIG. 3 depicts the plot of a soil sample containing pentachlorophenol as a contaminant. The lower absorbance line represents before light exposure absorbance, while the higher absorbance line represents post light exposure absorbance.

A system of TMPD reagent contacted with a sample solution of isopropyl alcohol contaminated with pentachlorophenol ("PCP") is shown in FIGS. 1–3. FIG. 1 demonstrates a method for determination of the maximally sensitive wavelength, namely 564 nm. The curves plotted in FIG. 1, in ascending order represent PCP concentrations of 0, 1.0, 5.1, 11.1, 22.2, and 44.3 ppm respectively. The light source used was a Black Ray model XX-15L (UVP Inc.). The lamp utilized two 15 watt bulbs that generate 1600 microwatts per square centimeter at a distance of 15 centimeters from the lamp. The spectrophotometer was a diode array spectrophotometer model 8452A (Hewlett Packard Co.).

FIG. 2 shows a plot of reference data. FIG. 2 illustrates light absorption data plotted as a function of PCP concentration. The plot of FIG. 2 is derived from the absorption spectra of FIG. 1 and may be used in the comparison step of the method to determine the presence of a quantity of PCP. The plot also shows how background data is tolerated. For instance, the data point at 0 ppm PCP concentration represents post-exposure background absorbance of 0.4 units.

FIG. 3 illustrates data generated from application of the method to a soil sample contaminated with PCP. The lower absorbance curve represents before light exposure absorbance, while the upper curve represents after light exposure absorbance. From FIG. 3, the light induced change in absorbance can be measured by calculating the difference between the before exposure curves and the after exposure curves at the optimized reference wavelength of 564 nm. This change in absorbance data, for the sample of FIG. 3 is in the range of 0.5 units. This 0.5 unit value is then compared to the reference plot of FIG. 2 to determine PCP concentration in the FIG. 3 sample. Referring back to FIG. 2, a change in absorbance of approximately 0.5 units on the y-axis corresponds to the reference value along the x-axis of the range of 40–50 parts per million. This means the sample of FIG. 3 contains 40–50 parts per million of PCP.

FIG. 2 illustrates that it is unnecessary to have a zero absorbance at zero contaminant level. During the comparison step, the absorbance at zero contaminant concentration reference is subtracted from the measured absorbance of the contaminated sample. In addition to this light induced background absorbance, a system may have background absorbance prior to light exposure. FIG. 3 illustrates that a sample need not have a zero absorbance before light exposure. The value used in comparing the absorbance data is the difference between before exposure and after exposure values. Like the zero contaminant, post exposure background, this pre-exposure background represented by the lower trace in FIG. 3 can be subtracted from the experimental value measured in the contaminated sample when comparing reference and sample light absorption data. Thus, the method is flexible enough to be applied to sample systems with pre-exposure absorbance. Post exposure absorbance changes in the absence of contaminant can also be tolerated, as the zero contaminant concentration point plotted in FIG. 2. illustrates.

EXAMPLE II

A preferred embodiment of the invention, using soil contaminated with polychlorinated biphenyl ("PCB") as a sample, comprises the steps of mixing a measured amount of the soil, for example a gram, with a measured amount of photodonor reagent, in this case 0.001M TMPD in acetonitrile. After thorough mixing, the sample and photodonor reagent solution slurry are poured through Whatman #4 filter paper, providing a solution of extracted sample and photodonor reagent. This extracted sample solution contains contacted reagent and solvent.

The extracted sample of contacted photodonor reagent solution is then exposed to a light source, in this case, an ultraviolet lamp with a maximum frequency of 365 nanometers. The appropriate time of exposure is dependant on the particular photodonor reagent and halogenated hydrocarbon used for reference comparison. In the sample contaminated with polychlorinated biphenyl ("PCB"), a light exposure of thirty minutes enabled differentiation of reference Eest samples consisting of known PCB concentrations of 0, 1, 2, 5, 10, 20, 40, and 80 part per million PCB in the test sample. The light induced absorption changes were observable in the 450 through 650 nanometer range.

EXAMPLE III

The present invention may be used for the detection and measurement of aromatic hydrocarbons such as naphthalene, anthracene, and pyrene by contacting samples contaminated with photoreactive aromatic hydrocarbons with a halogenated organic compound. A preferred embodiment of this method is illustrated by using the method of the present invention to contact a sample containing an amount of pyrene with a known concentration of carbon tetrachloride. Carbon tetrachloride is used in a similar manner as the reagent in the previous examples. Namely, it is used in a fixed concentration to generate reference data from various concentrations of aromatic hydrocarbon, in this case, pyrene.

Figure 6:
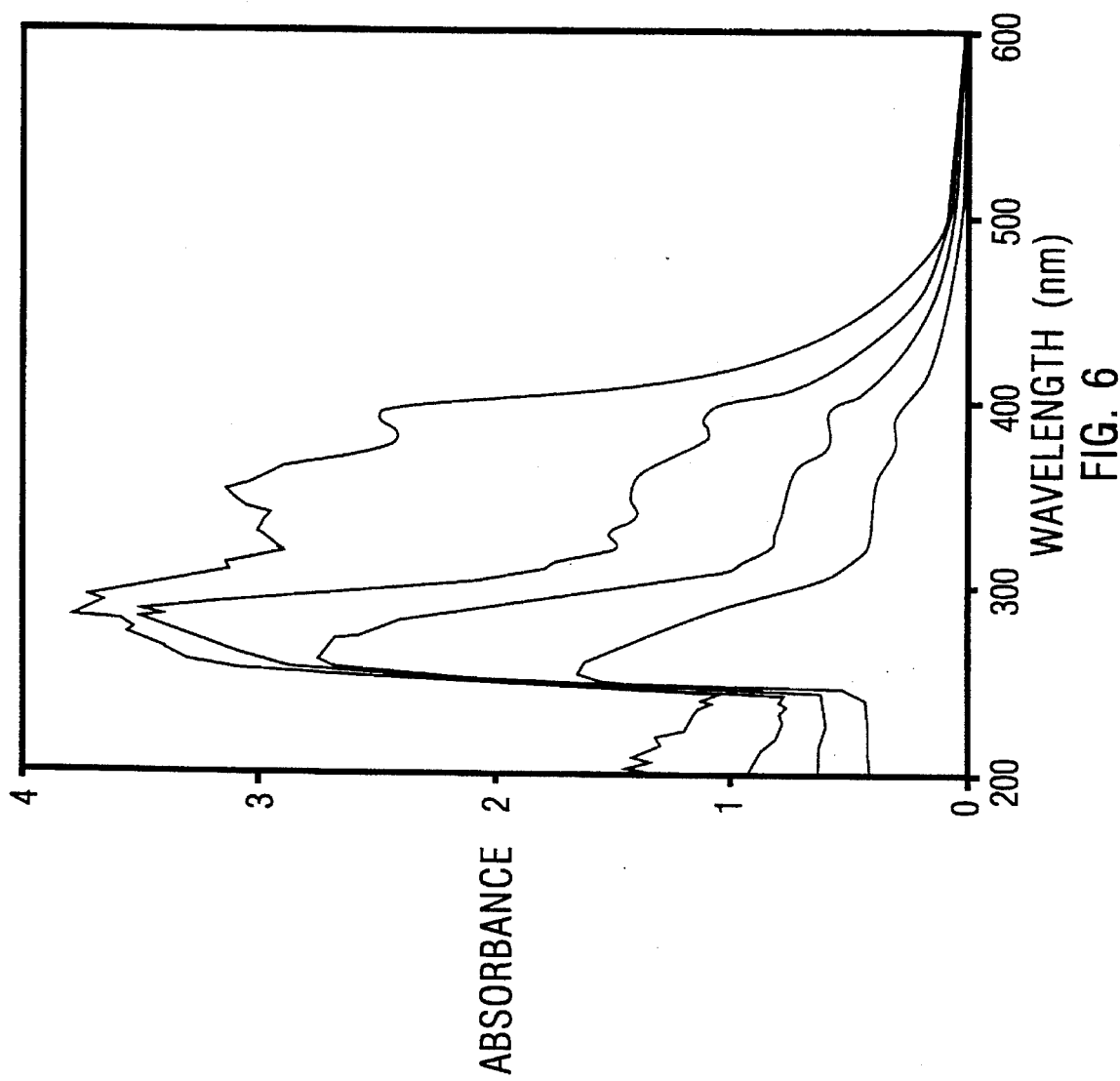
FIG. 6 depicts data from application of the method to a system using carbon tetrachloride as a reagent to quantify a sample contaminated with the polyaromatic compound pyrene. The traced lines in ascending order, represent pyrene in concentrations of 20, 40, 80, and 160 ppm respectively.

In FIG. 6, the reference samples included pyrene in concentrations of 20, 40, 80, and 160 parts per million. These samples were contacted with carbon tetrachloride. After light exposure of thirty minutes, the absorbance of the exposed samples increased in proportion to the pyrene concentration as shown by the four lines plotted in FIG. 6. The absorption change was observable in the 200 through 600 nanometer range. This reference data enables detection of pyrene concentrations in the 20–160 parts per million range. However, the method should not be limited to these concentrations. By increasing light exposure time, reference data for lower concentrations of pyrene could be generated.

In addition, various reagents may be used in the application described by this example. We have found that carbon tetrabromide is a suitable halogen for application of the method as applied in this example.

We have also discovered that the sensitivity to lower concentrations of pyrene contamination can be increased by adding a solvent, such as acetone or methanol, to the halogenated hydrocarbon system. We have found that solvent dielectric constant influences the sensitivity of the method and can be used to adjust the detection range of the method. For instance, acetone has a relatively high dielectric constant, and exhibits a predictable sensitivity increasing effect when used in the method of this example.

EXAMPLE IV

One of the present invention's significant advantages is that the method may be used to differentiate halogenated hydrocarbons. This differentiation application is enabled due to the differences in absorption curves produced when the method of the present invention is applied to differing classes of halogenated organic compounds. For instance, for a given reagent, the reference data produced when the method is applied to aromatic compounds is differentiable from the reference data produced from aliphatic compounds. When measured over a range of wavelengths, the reference data produces a characteristic signature shape, dependent on the class of contaminant. As in other applications of the invention, the magnitude of the measured absorption increase is dependent on the concentration of contaminant. The signature shape of the absorbance curve is dependent on the structure of the contaminant, and the particular reagent and solvents used.

Figure 4:
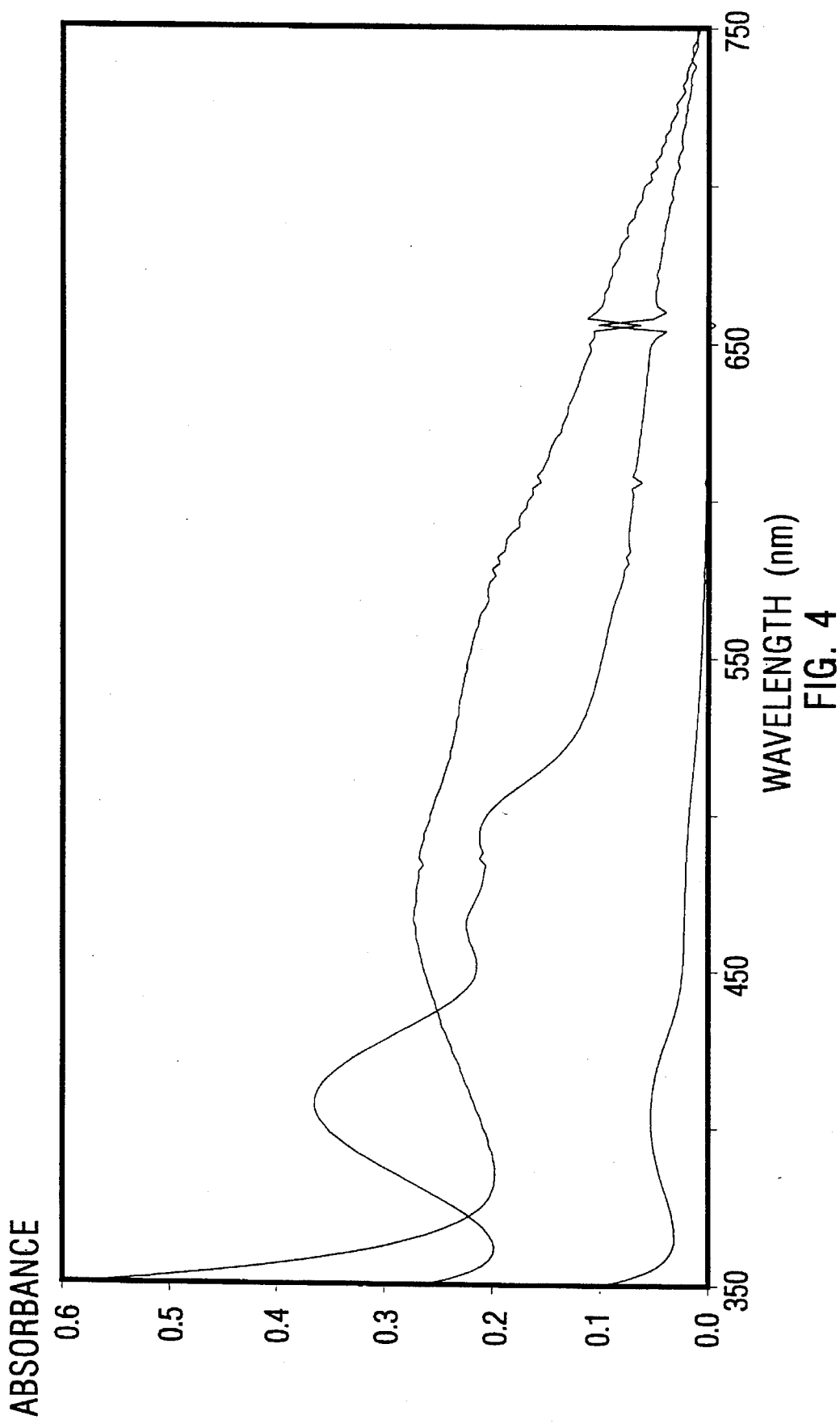
FIG. 4 depicts data from application of the method to a system consisting of 0.001M 1,4-phenylenediamine as a reagent, mixed in isopropyl alcohol. The line that shows the larger magnitude peak in the 400 nm wavelength area represents carbon tetrachloride as a contaminant. The middle line represents pentachlorphenol as the contaminant. The lower absorbance line represents a plot of the system in the absence of contaminant.
Figure 5:
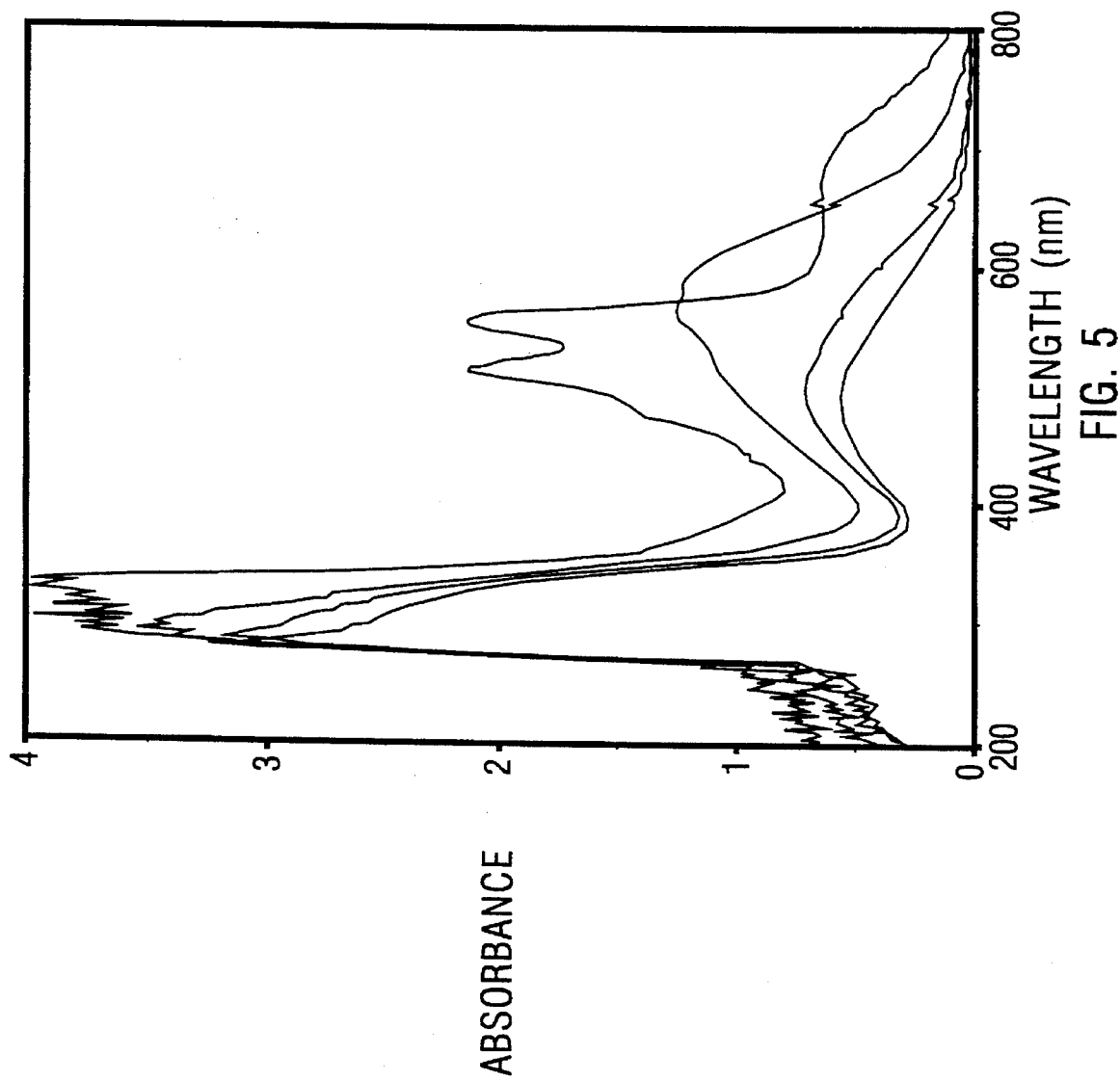
FIG. 5 depicts a reagent-solvent-contaminant system consisting of 0.001M N,N-diethyl-1,4-phenylenediamine as a reagent mixed in isopropyl alcohol contaminated with carbon tetrachloride. The carbon tetrachloride concentrations represented by the lines in ascending order are 0, 1, 10, and 100 parts per million.

This differentiation advantage is disclosed by an embodiment of the present invention that uses 1,4-phenylenediamine as a reagent. The method is applied to samples of isopropyl alcohol contaminated with carbon tetrachloride, an aliphatic compound. The method is applied in similar fashion using a sample contaminated with pentachlorophenol, a representative aromatic compound. Several differences in the absorption data are shown in FIG. 4. The lower absorbance line represents background absorption of the solvent-reagent system after exposure to light. The curve showing the largest peak in the 420 nm area represents 10 ppm carbon tetrachloride. The more gradual peak, showing increased absorbance in the range greater than 450 nm is representative of 1000 ppm pentachlorophenol (PCP). Several aspects of the invention are illustrated by this example. First, the maximum peak for carbon tetrachloride is at a much lower wavelength than for the aromatic compound. We have discovered that for a given reagent contacted with a specific contaminant a characteristic signature maximum absorption pattern is detectible. Secondly, the carbon tetrachloride peak is relatively more of a "spike", having a much narrower peak linewidth. In contrast, the aromatic compound data shows a more diffuse increase in absorbance over a larger range of wavelengths. The band of peak absorption has a larger linewidth. Both the peak wavelength and linewidth of the characteristic absorption changes can be used to identify selected unknown halogenated hydrocarbons of differing classes.

Figure 7:
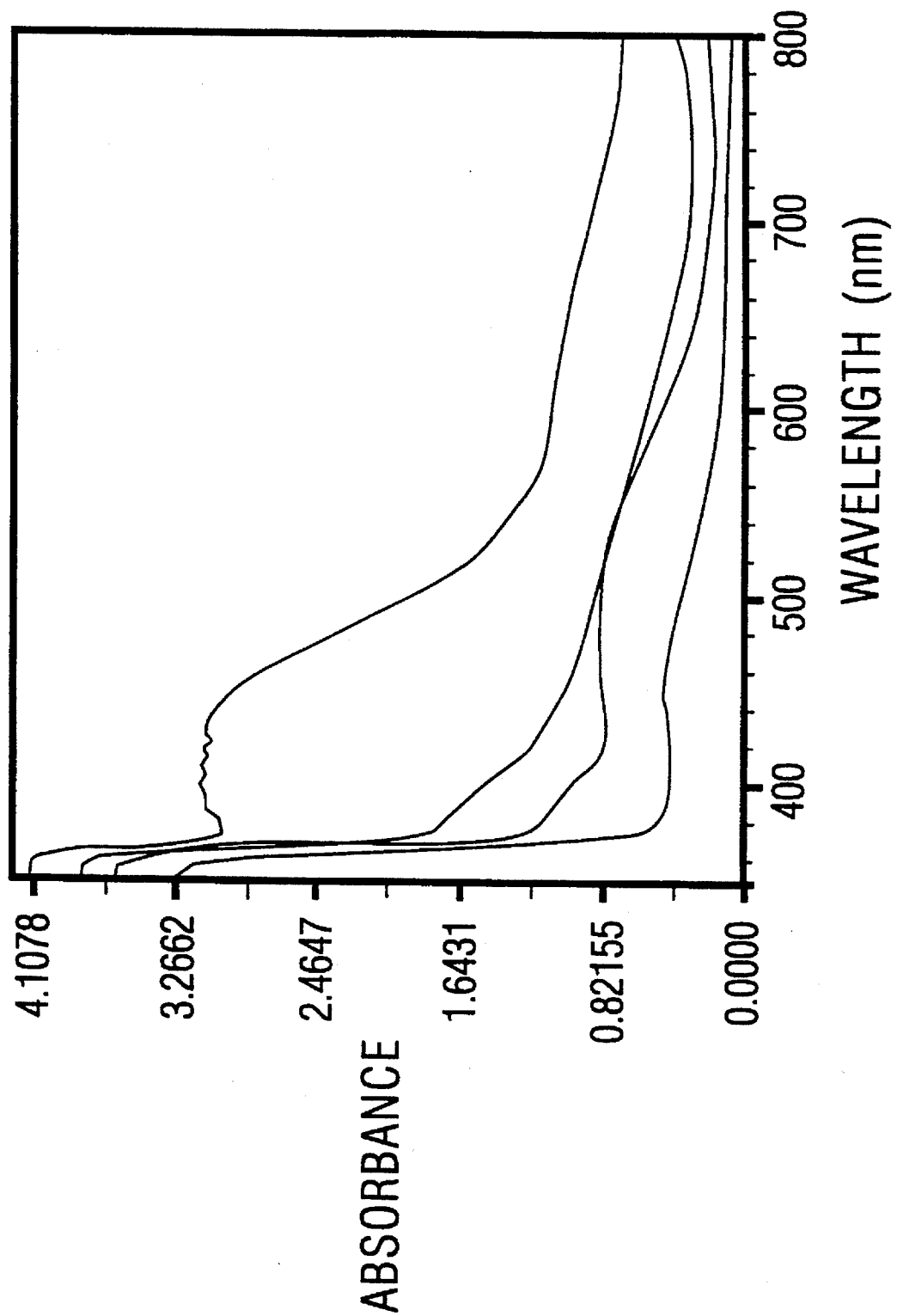
FIG. 7 depicts data from application of the method to a system using 2,7-diaminofluorene mixed in acetonitrile in 0.001M concentration. In ascending order, the traced lines represent samples containing no halogenated compound, pentachlorophenol, trichlorethylene, and carbon tetrachloride, all in concentrations of 10 ppm.

In a related application of the invention, FIG. 7 illustrates the method applied to various classes of halogenated compounds. This application used 0.001M 2,7-diaminofluorene in acetonitrile as a reagent-solvent system. The overlaid spectra show in ascending order of absorbance, reagent only with no contaminant, pentachlorophenol, trichloroethylene and carbon tetrachloride, all in 10 ppm concentrations of respective contaminant. The time of light exposure was 20 minutes. The size, location and linewidth of the peaks all illustrate signature differences in contaminant data.

EXAMPLE V

In an embodiment of the present invention based on the same principles as the basic method, the reagent may be associated with a solid support material, such as an inert plastic. This association may be a direct attachment of the reagent to the support material as in the case of polymers that act as reagents, such as poly(9-vinylcarbazole). Any physical association between reagent and binder that allows a known amount of reagent to be contacted with the sample is tolerable. This may range from uniform mixing of reagent and binder media to surface contact of reagent and media.

This embodiment of the invention may require doping of binder media with reagent prior to application of the method in order to disperse a known concentration of the reagent in the binder. If the binder allows the contaminant in the sample to contact the reagent while reagent is completely dispersed in the binder, the reagent may also be encapsulated in a binder media. This would be the case in solvent systems which allow penetration of the binder media by the contaminant. In order to facilitate observation of changes in absorbance, the preferred binder media is substantially transparent to light in the absorbance range of the reagent and contacted reagent.

A series of field tests may be made from reagents in varying concentrations associated with suitable solid media, such as an inert dipstick. Since color change in the system would be proportional to the concentration of a reagent, a characteristic color change for a given reagent concentration will represent a level of contamination. This would allow quick measurement of a threshold level of contaminant. By providing solid systems substantially unchanged when exposed to a given level of contaminant and systems which change at the contaminant level, the contaminant could be roughly measured.

Examples of binder media include polycarbonate, polystyrene, poly(methylmethacrylate) and polyamide. Certain binder materials act as a reagent without addition of other materials. For instance, poly(9-vinyl carbazole) or other electron donor polymers that are capable of color formation when contacted with halogenated materials could be used as reagent binder media.

In an application of this example, the reagent system could act as a permanent record of the test, so long as light exposure is controlled after contacting the system with contaminant.

EXAMPLE VI

This example illustrates the method of the present invention using 2,7-diaminofluorene as a reagent. The data generated by this example is illustrated in FIG. 7, an overlaid spectral plot of data generated from application of the method to various known contaminants. The time of light exposure was twenty minutes.

The reagent system has a low background level as shown by the lowest absorbance line plotted in FIG. 7. The background level varies slightly, depending upon the selected wavelength. Contaminants illustrated in FIG. 7 are carbon tetrachloride, shown in the highest absorbance plot; trichloroethylene in the next highest plot, and pentachlorophenol shown in the third highest plot. All contaminants were in concentrations of ten parts per million. The data illustrated discloses different maximum absorption wavelengths for each contaminant, and different signature shapes in the plotted data curve for each contaminant.

In order to apply the method to detect the quantity of a halogenated hydrocarbon, a range of known reference are analyzed to generate reference data. Adjustments in the time of exposure and solvents used to extract or dilute the sample may be used to refine the detection levels of the method. For example, the solvent chosen to dissolve the reagent may increase the absorption change after exposure. In addition the time of exposure may be increased to increase absorption change of a given concentration of contaminant. Dilution of the sample, either before or after contact with reagent facilitates detection of higher levels of halogenated hydrocarbon or aromatic compounds.

EXAMPLE VII

We have discovered the method of the present invention may be applied to water samples contaminated with halogenated organic compounds. The reagent 2,7-diaminofluorene in a 0.1 mM concentration, mixed in isopropyl alcohol (IPA) was contacted with water samples contaminated with trichlorethylene, pentachlorophenol, and carbon tetrachloride. This enabled detection of 200 ppm of trichloroethylene in the sample after 10 minutes exposure to ultraviolet light.

Due to the relatively low absorbance nature of the IPA-water solvent system, no separation or extraction step was required, although an extraction step could be used to analyze multi-phase systems with known compositions. By analyzing an extracted sample and applying a known partition coefficient, the method could be combined with extraction to determine the concentration of contaminant in a sample indirectly.

While the invention has been described in detail with respect to specific preferred embodiments of the present invention, variations and modifications are comprehended to be included in the disclosed invention. For example, the method is applicable to both fixed wavelength point absorbance determinations and comparisons over a range of wavelengths. In addition, the method may be practiced in a laboratory setting or as a field test, depending on the means used for measuring changes in the indicator reagent system, including visual inspection of color changes. In this and other ways, the invention may be embodied in other specific forms without departing from its spirit or essential characteristics. The described embodiments are to be considered in all respects as only illustrative, and not restrictive. The scope of the invention is, therefore, indicated by the appended claims, rather than the foregoing description. All changes which come within the meaning and range of equivalency of the claims are to be embraced within their scope.

We claim:

1. A method for quantifying photoreactive aromatic compound in a sample, said method comprising:

(a) contacting a polyhalogenated organic compound selected from the group consisting of carbon tetrachloride and carbon tetrabromide with said photoreactive aromatic compound to form a contacted photoreactive aromatic compound;

(b) exposing said contacted photoreactive aromatic compound to ultraviolet light sufficient to produce change in the optical absorption of said contacted photoreactive aromatic compound;

(c) determining the light absorption data for said contacted photoreactive aromatic compound; and (d) comparing said light absorption data of said contacted photoreactive aromatic compound to reference data for said photoreactive aromatic compound to quantify said photoreactive aromatic compound;

wherein said light absorption data is measured at at least one wavelength at which said change in optical absorption of said contacted photoreactive aromatic compound is substantially maximized, and wherein said at least one wavelength is longer than the wavelength at which the optical absorption of said photoreactive aromatic compound is greatest.

2. A method for quantifying a photoreactive aromatic compound as in claim 1, wherein said polyhalogenated organic compound is carbon tetrachloride.

3. A method for quantifying a photoreactive aromatic compound as in claim 1, wherein said polyhalogenated organic compound is carbon tetrabromide.

4. A method for quantifying a photoreactive aromatic compound as in claim 1, wherein said photoreactive aromatic compound is contacted with a solvent.

5. A method for quantifying a photoreactive aromatic compound as in claim 1, further comprising the step of separating said photoreactive aromatic compound from the sample following step (b) and prior to step (c).

* * * * *